United States Patent [19]

Kalopissis et al.

[11] 3,950,542

[45] Apr. 13, 1976

[54] CYSTEAMINE DERIVATIVES FOR ORAL TREATMENT OF SEBORRHEA

[75] Inventors: Gregoire Kalopissis; Georges Manoussos, both of Paris, France

[73] Assignee: L'Oreal, Paris, France

[22] Filed: May 9, 1974

[21] Appl. No.: 468,595

Related U.S. Application Data

[60] Division of Ser. No. 140,956, May 6, 1971, Pat. No. 3,821,405, which is a continuation-in-part of Ser. Nos. 706,652, Feb. 19, 1968, Pat. No. 3,629,452, and Ser. No. 801,154, Feb. 20, 1969, abandoned.

[30] Foreign Application Priority Data

| Feb. 21, 1967 | Luxemburg | 53029 |
| Feb. 20, 1968 | Luxemburg | 55522 |
| Apr. 23, 1971 | Luxemburg | 63056 |
| Apr. 23, 1971 | Luxemburg | 63057 |

[52] U.S. Cl...... 424/316; 260/293.85; 260/294.8 F; 260/294.8 G; 260/294.8 R; 260/326.84; 260/470; 260/479 S; 260/481 R; 260/501.19; 260/501.21; 260/515 M; 260/518 A; 260/518 R; 260/534 C; 260/534 E; 260/534 G; 260/534 S; 260/553 E; 260/558 H; 260/558 S; 260/570.5 S; 424/DIG. 4; 424/319; 424/320; 424/321; 424/324; 424/325; 424/330

[51] Int. Cl.$^2$................................ H61K 31/205
[58] Field of Search.............. 424/DIG. 4, 316, 325

[56] References Cited

UNITED STATES PATENTS

| 2,769,839 | 11/1956 | Fincke | 260/570.5 |
| 2,835,704 | 5/1958 | Walton | 260/562 |

*Primary Examiner*—Stanley J. Friedman
*Assistant Examiner*—Vera C. Clarke
*Attorney, Agent, or Firm*—Cushman, Darby & Cushman

[57] ABSTRACT

A method for treating a scalp characterized by an excessive secretion of sebum, to improve the condition thereof by reducing said excessive secretion comprising orally administering to a human being having a scalp so characterized a therapeutic composition comprising an ingestible carrier admixed with, as a nontoxic active compound, cysteine or cysteamine derivatives, the active compound is present in amounts of about 0.75–3 weight percent of the composition which is administered at a rate of about 1–5 mg/kg/day based on the weight of the human being during a period of about 15 days.

2 Claims, No Drawings

CYSTEAMINE DERIVATIVES FOR ORAL TREATMENT OF SEBORRHEA

This is a division of application Ser. No. 140,956, filed May 6, 1971, now U.S. Pat. No. 3,821,405, which is a continuation-in-part of our earlier applications Ser. No. 706,652, filed Feb. 19, 1968, now U.S. Pat. No. 3,629,452 and Ser. No. 801,154 filed Feb. 20, 1969, now abandoned.

The present invention relates to a method for treating a scalp characterized by an excessive secretion of sebum, to improve the condition thereof by reducing said excessive secretion comprising orally administering to a human being having a scalp so characterized a therapeutic composition comprising an ingestible carrier admixed with, as a non-toxic active compound, certain cysteine or cysteamine derivatives.

The active compound employed in the present invention is selected from the group consisting of a compound having the formula

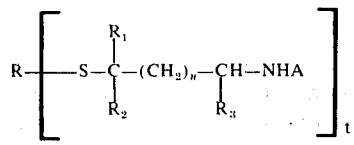

and the acid salts thereof, wherein $n$ is 0 or 1 and when $n$ is 0, $R_1$ and $R_2$ are selected from the group consisting of hydrogen and $CH_3$ and when $n$ is 1, $R_1$ and $R_2$ are hydrogen;

$R_3$ is selected from the group consisting of hydrogen and $-COR_7$ wherein $R_7$ is selected from the group consisting of hydroxy, alkoxy containing 1–5 carbon atoms, glucosamine, $-NH-NH_2$, $-NHOH$,

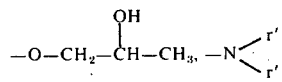

wherein $r'$ represents a member selected from the group consisting of hydrogen and alkyl having 1–3 carbon atoms,

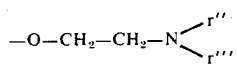

wherein $r''$ and $r'''$ each independently represent alkyl having 1–3 carbon atoms or together with the nitrogen atom to which they are attached form a ring selected from the group consisting of morpholine, piperidine, pyrrolidine and N'-methylpiperazine;

A is selected from the group consisting of hydrogen, $-CONH_2$, nicotinoyl, glutamyl, $-COR_4$ and $-SO_2R_6$ wherein $R_4$ is selected from the group consisting of hydrogen, alkyl having 1–18 carbon atoms, alkenyl having 2–18 carbon atoms,

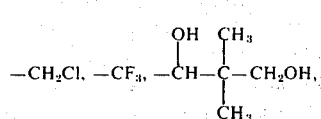

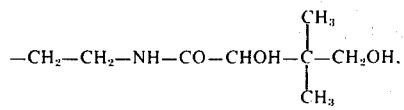

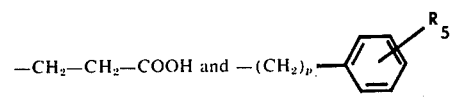

wherein $p$ is 0–1 and $R_5$ is selected from the group consisting of hydrogen, alkyl having 1–4 carbon atoms, alkoxy having 1–4 carbon atoms, halogen and acetamide, and wherein $R_6$ is selected from the group consisting of alkyl having 1–4 carbon atoms and

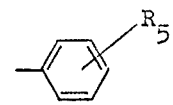

wherein $R_5$ has the meaning given above, $t$ is 1 or 2 and when $t$ is 1, R is selected from the group consisting of linear or branched chain alkyl having 1–18 carbon atoms, alkenyl having 3–18 carbon atoms, propyne-2 yl, mono- or dihydroxyalkyl containing 2–4 carbon atoms, 1,2-dichlorovinyl, $-C(C_6H_5)_3$, $-C(CH_3)_3$, $-CH(C_6H_5)_2$, $-CH(C_6H_4\ p\text{-}OCH_3)_2$, $-C(CH_3)_2(C_6H_4\ p\text{-}OCH_3)$, $-CONH_2$,

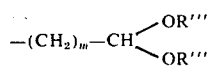

wherein $R'''$ is alkyl having 1–4 carbon atoms and $m$ is 1–2,

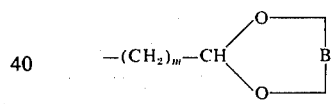

wherein $m$ is 1–2 and B is selected from the group consisting of

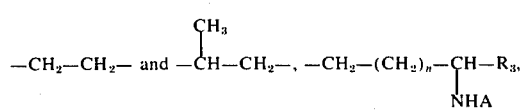

wherein $n$, $R_3$ and A have the meanings given above, $-(CH_2)_s-COR_{10}$ wherein $s$ is 1–5 and $R_{10}$ is selected from the group consisting of $R_7$, piperidino, morpholino, pyrrolidino, N'-methylpiperazino and $-N(CH_2-CH_2OH)_2$, $-(CH_2)_z-R_8$ wherein $z$ is 0, 1 or 2 and when $z$ is 0, $R_8$ is selected from the group consisting of naphthyl-1, napthyl-2, pyridyl-2, pyridyl-2 substituted with a member selected from the group consisting of nitro and alkyl having 1–4 carbon atoms, and pyridyl-2-N oxide when $R_3$ is hydrogen, and when $z$ is 1, $R_8$ is selected from the group consisting of naphthyl-1, naphthyl-2, thienyl-2, tetrahydrofuryl-2, furyl-2, pyridyl-2, pyridyl-2 substituted with a member selected from the group consisting of nitro and alkyl having 1–4 carbon atoms, and pyridyl-2-N-oxide and when z is 2, $R_8$ is selected from the group consisting of pyridyl-2, pyridyl-2 substituted with a member selected from the group consisting of nitro and alkyl having 1–4 carbon atoms and pyridyl-2-N-oxide, and

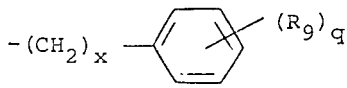

wherein $x$ is 0–2 and wherein when $q$ is 1, 2 or 3, $R_9$ is selected from the group consisting of hydrogen, halogen, alkoxy having 1–5 carbon atoms and linear or branched chain alkyl having 1–4 carbon atoms, and when $q$ is 1, $R_9$ is selected from the group consisting of acetamido, amino, phenoxy, cyclohexyl, methylenedioxy, trifluoromethyl, nitro, phenyl, dialkylamino wherein each alkyl moiety has 1–5 carbon atoms, alkylthio having 1–5 carbon atoms, alkylsulfinyl having 1–5 carbon atoms and alkyl-sulfonyl having 1–5 carbon atoms, and when $t$ is 2, R is selected from the group consisting of alkylene having 2–4 carbon atoms, alkylene having 2–4 carbon atoms and substituted with 1–2 hydroxy groups, butenylene and —$(CH_2)_2$—$SO_2$—$(CH_2)_2$—.

When the above active compounds contain at least one primary amine group, they are preferably used as salt with an inorganic or organic acid selected from the group consisting of hydrochloric, hydrobromic, sulfuric, phosphoric, p-toluene sulfonic, dihydrocinnamic, cinnamic, mandelic, salicylic, tropic, oxalic, malic, tartaric, succinic, acetic, lactic, 3-hydroxy butyric, fumaric, undecylenic, phenylacetic, monochloroacetic, trichloroacetic, glycolic, nicotinic, p-aminobenzoic, glutamic, aspartic, citric, pentothenic, crotonic acid and ascorbic.

However, when the active compounds carry both an amine group and a carboxylic acid function it must be used in order to break the internal salt an inorganic acid or a strong organic acid such as p-toluenesulfonic acid or trichloracetic acid.

In a related embodiment of the present invention the active compound is selected from the group consisting of a compound having the formula:

1.

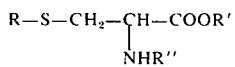

wherein R is selected from the group consisting of —$C(C_6H_5)_3$, —$CH(C_6H_5)_2$, —$CH_2$—$C_6H_5$ and —$(CH_2)_n$—$COOR'$ wherein $n$ is 1–4, R' is selected from the group consisting of hydrogen and —$CH_3$ and R'' is selected from the group consisting of hydrogen and —$COCH_3$;

2. the hydrochloride of the compound in (1) above;
3. a compound having the formula

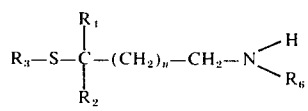

wherein $R_1$ and $R_2$ are each hydrogen; $n$ is 0 or 1; $R_3$ represents —$(CH_2)_p$ — $R_4$ wherein $p$ is 0, 1 or 2 when $p = 0$, $R_4$ is selected from the group consisting of: $C_6H_5$, —$C(CH_3)_3$ — $C(C_6H_5)_3$ and

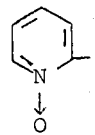

when $p = 1$, $R_4$ is selected from the group consisting of: $C_6H_5$, —$COOR_5$ in which $R_5$ represents hydrogen,

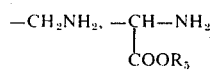

in which $R_5$ is hydrogen,

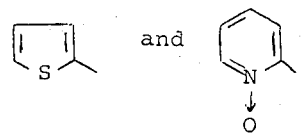

when $p = 2$, $R_4$ is selected from the group consisting of: $C_6H_5$, —$COOR_5$ in which $R_5$ represents hydrogen,

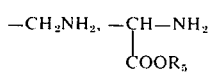

wherein $R_5$ is hydrogen and

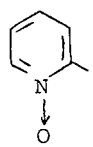

$R_6$ represents a member selected from the group consisting of hydrogen and —$COCH_3$; and 4. the organic and inorganic acid salts of the compound in (3) above, said active compound being present in an amount ranging from 0.75 to 3 percent, preferably 0.75 to 1.5 percent, by weight, of said composition.

The organic or inorganic acids useful to prepare the active compound in salt form are hydrochloric, hydrobromic, salicylic, paratoluene sulfonic, citric, phosphoric, malic, tartaric, nicotinic and ascorbic acids.

In another related embodiment of the present invention, the active compound has the formula

wherein R is selected from the group consisting of alkyl, substituted alkyl, wherein the alkyl moiety has 1–18 carbon atoms, alkenyl wherein the alkyl moiety has 3–18 carbon atoms, propyne-2 yl and mono and dihydroxy alkyl wherein the alkyl moiety is 2–4 carbon atoms and Z is selected from the group consisting of hydrogen, —COR' and —$SO_2R''$ wherein R' is selected from the group consisting of lower alkyl having 1–6 carbon atoms, phenyl, benzyl and tolyl and R'' is selected from the group consisting of lower alkyl having 1–4 carbon atoms, phenyl and tolyl, and the non-toxic acid salts thereof. Acids usefully employed to produce such salts include hydrochloric, phenylacetic, undecylenic and sorbic acids.

The active compounds of this invention may be dissolved in a alimentary liquid, such as an aqueous or hydro-alcoholic solution which may be aromatized.

They may also be incorporated into any injectable pharmaceutical excipient. They may then take, for example, the form of granulas, pills or tablets. Examples of such compoundings are described in the U.S. Pat. No. 2,888,380.

The composition of this invention is administered at a rate of 1–5 mg/kg/day based on the weight of the human being and is generally administered during a period of about 15 days. After 15 days, the treatment may be stopped and then resumed 15 days later.

METHOD OF PREPARATION

In a general manner, active compounds of the present invention can be prepared by the reaction of a thiol, with an organic halide or with an ester of methane sulfonic acid of p-toluene sulfonic acid (Method I), or with a compound having a reactive double bond (Method II), or with an oxirane (Method IV), or with an alcohol (Method III) or with ethylene imine and its acylation and sulfonylation derivatives (Method IV).

Method I

The most commonly employed procedure is the substitution reaction of essentially an equimolar ratio of a thiol with an organic halide or a methane sulfonate or a p-toluene sulfonate. The thiol can be aminated or not. The reaction is carried out under conditions generally or conventionally employed for nucleophilic substitutions including, for instance, a temperature ranging from 10° to 100°C, atmospheric pressure, and employing a solvent such as water, ammonia, alcohol or dimethyl formamide in the presence of a base such as an alkali or alkaline earth hydroxide, or carbonate, an alcoholate, an alkali or alkaline earth amide or even a tertiary aliphatic amine such as triethylamine according to the following general reaction:

R — X + R' — SH → R — S — R' + XH
(X = halogen or —OSO$_2$CH$_3$ or —OSO$_2$C$_6$H$_5$)
or
R' — X + R — SH → R' — S — R + XH The thiol R—SH or R'—SH can be prepared in situ by basic hydrolysis of an isothiouronium salt according to the following general reaction:

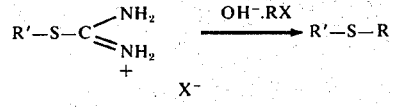

Method I (alternative)

When R is an aryl radical (X=0), the halide employed is an aryldiazonium halide (Vigneaud et al, J.Biol. Chem., 1941, 138, 369 and Clarke and Inouye, J.Biol.Chem. 1931, 94.541) and the reaction follows the general equation:

ArN$_2$CL+R'—SH → Ar—S—R'+N$_2$+HCl

Method II

The addition reaction of essentially an equimolar ratio of a thiol with a compound having a reactive double bond is well known and can be carried out, in accordance with known procedures, without a catalyst or in the presence of a peroxide such as ascaridole, benzoyl peroxide, azo bis-isobutyronitrile, or in the presence of a base such as those employed in Method I, or even a quaternary ammonium hydroxide or a secondary amine such as piperidine. Representative reaction temperatures include 10° to 100°C and at atmospheric pressure.

The reaction is most generally effected in a medium such as alcohol, for instance, lower alkanol, water, dioxane, alone or in admixture, with a basic catalyst, so as to obtain a small quantity of thiolate to initiate the reaction.

The compound utilized having a reactive double bond does not have an amine function. It can, however, contain an amide or sulfonamide function.

The radical R can originate from either a compound having a reactive double bond (scheme 1) or from a thiol (scheme 2) when R$_3$ and A are other than hydrogen.

Scheme 1

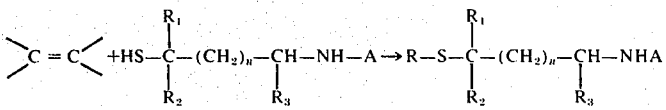

Scheme 2

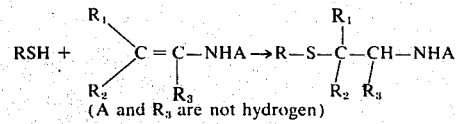

(A and R$_3$ are not hydrogen)

Method III

The compounds of the present invention, in which the sulfure atom is linked to a disubstituted or trisubstituted carbon atom, or to a benzyl or allyl radical, can conveniently be prepared at a temperature ranging from about 50° to 150°C and at atmospheric pressure by reaction of essentially equimolar amounts of a corresponding tertiary or secondary, benzyl or allyl alcohol, with a thiol, in the presence of a strong acid such as gaseous hydrochloric acid, p-toluene sulfonic acid, or a Lewis acid such as the etherate of boron trifluoride, in accordance with the following general reaction:

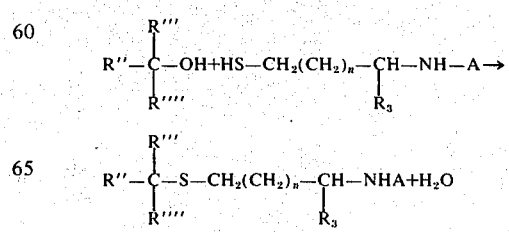

R''' and R'''' only represent hydrogen when R'' represents aryl or vinyl.

Method IV

Another particularly useful method for preparing compounds of the present invention consists of reacting essentially equimolar amounts of a thiol with an ethylene imine or an acylation or N-sulfonylation derivative thereof at a temperature ranging from about −30° to 80°C. at ambient or atmospheric pressures according to the following equations which provide an easy method of producing the following compounds:

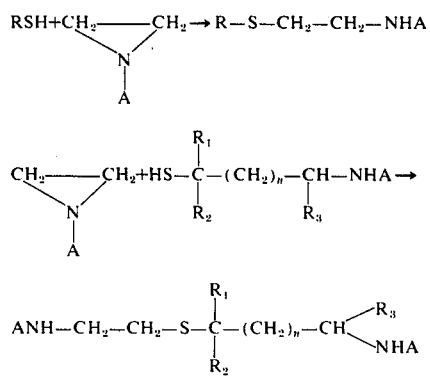

The reaction is made very easily, in a variety of solvents, chosen as a function of the solubility of the starting materials. Representative solvents include alcohols of low molecular weight and chloroform.

Method IV (alternate)

The β-hyroxythioethers can be prepared by an analogous procedure, by replacing the azinidine by an oxiran, and by effecting the reaction in a polar medium with a basic catalyst, as in Method I according to the following scheme:

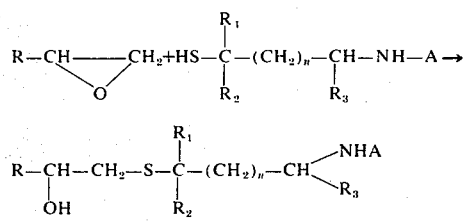

In addition to the above methods, the esters and the amides of the present invention can be prepared starting with other compounds.

Thus, esters can be obtained starting with the corresponding acide ($R_7 = OH$), by reacting an appropriate alcohol therewith to give the desired ester, either at an elevated temperature in the presence of a mineral or sulfonic acid, or at a low temperature in the presence of thionyl chloride (Method V).

Amides included in the meaning of $R_3$ can be prepared simply by the reaction of ammonia, hydrazine, hydroxylamine or an appropriate amine on the ester noted above, at a temperature generally lower than 30°C (Method VI).

The amides included in A can be conveniently prepared by the action of a halide or anhydride of a carboxylic acid to produce a carboxamide or by the action of a sulfonyl halide to produce a sulfonamide when the amide is formamide, the amide is prepared by action of formic acid. The reaction conditions most generally utilized are those of Schotten-Baumann, i.e., in water, in the presence of an alkaline hydroxide, or their rearrangement in an organic medium (aromatic hyrocarbon, generally a chlorinated solvent) in the presence of a base such as pyridine or a tertiary amine, for example, trialkylamine (Method VII).

When it is desired to prepare acylated compounds having an alcohol function, they can be obtained by the action of an amine on a lactone, the reaction being catalyzed by an alkaline alcoholate.

In the case of substituted acetamides, acetylation of the amine can often advantageously be effected by means of acetic anhydride in an acetic acid medium in the presence of concentrated sulfuric acid.

It will be noted, however, that the majority of the amides included in the meaning of A are in addition easily produced by one or more of Methods I–IV.

Finally, compounds of the type where A equals —$CONH_2$ are prepared by the action, in an aqueous or aqueous alcoholic medium, of an alkaline cyanate on a compound of the type A=H, in the presence of an equivalent amount of mineral acid, preferably, hydrochloric acid (Method VIII), the starting compound being obtained according to Methods I–IV.

The preparation of the salts of the active compounds is generally carried out by first dissolving the acid in an appropriate solvent and then pouring to this solution either a solution of the active compound in the same solvent or the active compound alone. The solvent must not be a solvent of the salt.

To prepare hydrochlorides, it is more convenient to dissolve the active compound in an appropriated solvent and then to bubble in the solution a slight stream of hydrogen chloride.

Representative Examples of Preparing Active Compounds According to the Foregoing General Reactions

EXAMPLE 1

N-(2-benzylthioethyl)nicotinamide: (Method VII)

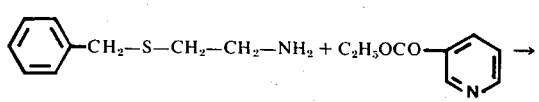

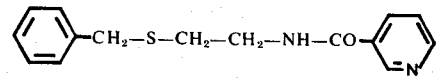

30 grams of ethyl nicotinate and 80 grams of 2-benzylthio ethylamine are heated for 12 hours at 170°–180°C. The ethane liberated during the reaction is removed by means of a Dean Stark apparatus. After cooling, the reaction mixture is dissolved in 400 cc of carbon tetrachloride; by addition of petroleum ether, the N-(2-benzylthioethyl)nicotinamide crystallizes: 47 g. By crystallization in a mixture of carbon tetrachloride and cyclohexane, there is recovered colorless crystals of the above product melting at 79°C.

| Analysis: | N | S |
|---|---|---|
| Calculated, % | 10.3 | 11.8 |
| Found, % | 10.4 | 11.9 |

By bubbling HCl gas into an acetone solution of the above product, the hydrochloride thereof is recovered, which melts at 135°C.

EXAMPLE 2

5-p-toluenesulfonamido 3-thia hexanedioic acid:

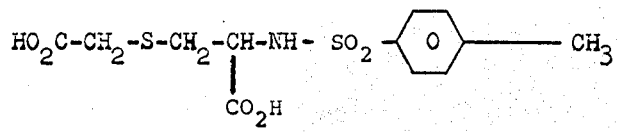

17.9 grams of 3-carboxymethylthio alanine are dissolved in 200 cc of normal soda. There are added under agitation 24 grams of p-toluene sulfonyl chloride then, in 3 hours, 100 cc of normal soda. The suspension is agitated again for 5 hours at ambient temperature, then filtered. The filtrate, acidified with HCl, is extracted with ethyl acetate. After evaporation of the ethyl acetate, there remains a yellow solid which crystallizes in water. 20 grams of the above product in crystalline form are obtained having a melting point of 152°C.

| Analysis: | C | H | S |
|---|---|---|---|
| Calculated, % | 43.23 | 4.53 | 19.23 |
| Found, % | 43.19 | 4.48 | 19.24 |

EXAMPLE 3

2-(2-p-toluenesulfonamido ethylthio)pyridine N-oxide (Method VII)

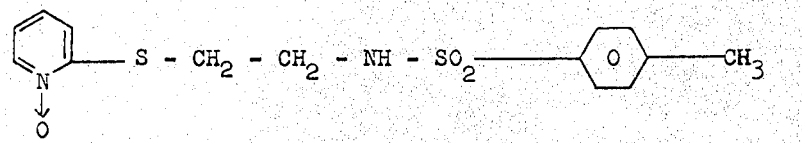

To a solution of 4.12 g of 2-β-aminoethylthio pyridine N-oxide hydrochloride in 60 cc of water, there are added 4 cc of 5N soda, then 3.8 g of p-toluenesulfonyl chloride. The mixture is agitated for 5 hours at ambient temperature. The pH is maintained a 9.5 by the addition of normal soda. The precipitate is filtered and crystallized in aqueous ethanol. Yield = 88%. Fusion point: 201°C.

| Analysis: | N | S |
|---|---|---|
| Calculated, % | 8.64 | 19.77 |
| Found, % | 8.77 | 19.85 |

EXAMPLE 4

3-(2-pyridyl methylthio) alanine (Method I)

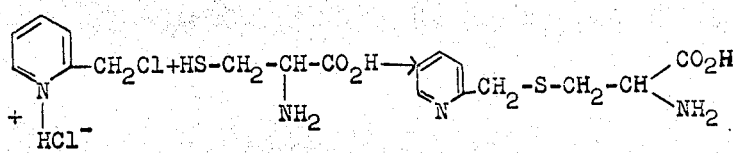

There are added, over a 15 minute period, 96 cc of 10 N soda to an aqueous solution of 54 g of cysteine hydrochloride. The solution obtained is treated by a cation exchange resin and the product absorbed on the resin is liberated with an ammoniacal solution. The eluate is evaporated and the residue is crystallized in a mixture of methanol and isopropyl ether. There is thus recovered 49 g of whitish crystals melting at 190°C.

| Analysis: | N | S |
|---|---|---|
| Calculated, % | 13.26 | 15.10 |
| Found, % | 13.23 | 15.32 |

EXAMPLE 5

3-o-chlorobenzylthio alanine and the corresponding methyl ester (Method I).

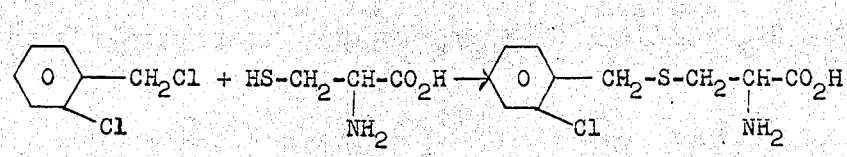

In 400 cc of ethanol containing 6.9 g of sodium, there are introduced 15.75 g of cystein hydrochloride, then a solution of 16 g of o-chlorobenzyl chloride in 20 cc of ethanol. The mixture is heated for 1 hour at 50°C. After cooling, there are added 400 cc of water and 30 cc of acetic acid. The product crystallizes and is filtered and washed with water. Yield: 20.8 g. Fusion point is 220°C.

| Analysis: | C | H | N |
|---|---|---|---|
| Calculated, % | 48.87 | 4.92 | 5.70 |
| Found, % | 48.61 | 4.68 | 5.42 |

15 grams of the product obtained above are put into suspension in 15 cc of methanol, in which there is bubbled a stream of dry gaseous HCl for 30 minutes. The reaction mixture is left standing for 2 hours at ambient temperature, evaporated to dryness, the oily residue being dissolved in 30 cc of methanol. The product is crystallized by the addition of diethyl oxide. Yield = 90%. Fusion point 150°C.

| Analysis: | C | H | N |
|---|---|---|---|
| Calculated, % | 44.60 | 5.10 | 4.72 |
| Found, % | 44.52 | 5.32 | 4.65 |

EXAMPLE 6

2,2'-thio diethylurea (Method I and VII) Method I:

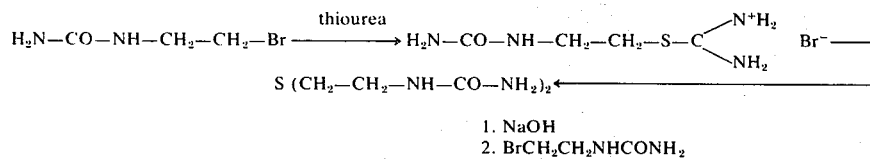

There are heated under reflux for 30 minutes, 66.3 g of thiourea and 145.6 g of β-bromoethylurea in 600 cc of isopropanol. The precipitate (185 g) is filtered, washed with isopropanol and dissolved in 900 cc of water. There is added to this solution during a 15 minute period, a solution of 30.45 g of soda in 150 cc of water and the resulting mixture is heated in a boiling water-bath for 1 hour under nitrogen. The water bath is removed and there is again introduced 150 cc of a soda solution (30.45 g soda), then a solution of 127.15 g of β-bromoethylurea in 150 cc of water.

The reaction mixture is left standing overnight at ambient temperature. The crystallized product is then filtered, yielding 126 g of white product melting at 234°C. Method VIII:

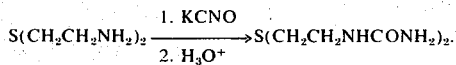

To a solution of 92.4 g of 2,2'thio diethylamine in 70 cc of water, there is added with agitation 133 cc of 11.6 N hydrochloric acid while cooling so as to maintain the temperature below about 25°C. Then there is added sufficiently rapidly, a solution of 127 g of potassium cyanate (98%) in 150 cc of water. The reaction mixture is left standing overnight and the resulting precipitate is filtered, dried and crystallized in water, yielding 128 g of white crystals, the fusion point of which is 234°C.

| Analysis: | N | S |
|---|---|---|
| Calculated, % | 27.18 | 15.53 |
| Found, % | 27.15 | 15.32 |

EXAMPLE 7

3,3'(1,4 dithio butene-2-diyl)dialanine (Method I)

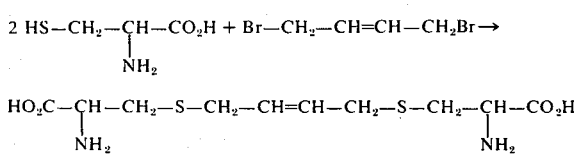

There is added dropwise a solution of 21.4 g of 1,4 dibromo butene-2 in 200 cc of ethanol to a solution of 35.10 g of the hydrochloride of cysteine monohydrate and 40 cc of 10 N soda in 200 cc of water and 300 cc of ethanol. The mixture is agitated for 6 hours at ambient temperature. The precipitate which forms is filtered and crystallized in a mixture of methanol and water. There is obtained a yield of 97% of a white solid.

| Analysis: | C | H | N |
|---|---|---|---|
| Calculated, % | 40.79 | 6.16 | 9.51 |
| Found, % | 40.74 | 6.23 | 9.23 |

EXAMPLE 8

3-β-ureidoethylthio alanine (Method I)

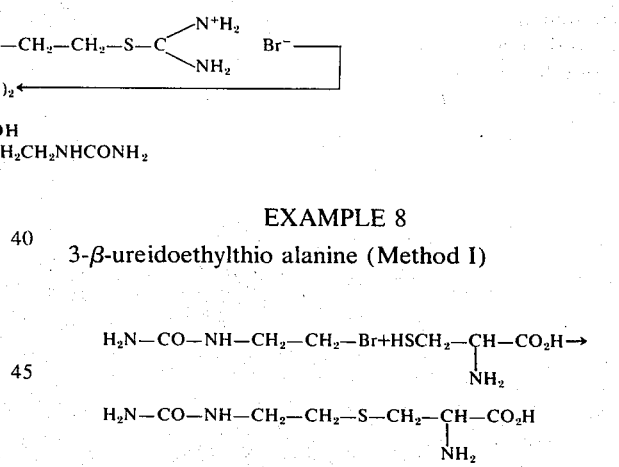

26.25 g of cysteine hydrochloride and 27.83 g of βbromoethylurea are dissolved in 150 cc of water under nitrogen. A solution of 13.35 g of soda in 30 cc of water is added during a 40 minute period and the mixture is heated for 3 hours at 50°C. After cooling, there is added to the solution, 4 times its volume of water and the resulting mixture is passed over a cation exchange resin. After washing with water, the product fixed on the resin is eluted with an ammoniacal solution. The eluate is evaporated to dryness and the residue is crystallized in an aqueous methanol solution. There are obtained 19.5 grams of the white product melting at 220°C with decomposition.

| Analsysis: | C | H | S |
|---|---|---|---|
| Calculated, % | 34.80 | 6.28 | 15.46 |
| Found, % | 34.84 | 6.20 | 15.62 |

EXAMPLE 9

3-(4-methoxycarbonylbutylthio)alanine hydrochloride (Method I)

$$CH_3OCO(CH_2)_4-S-CH_2-CH(NH_2 \cdot HCl)-CO_2H$$

To a solution of 8.77 g of cysteine hydrochloride monohydrate in 150 cc of methanol, there are added, successively, 7.6 g of potassium, then, during a 30 minutes period, 10.45 g of methyl ω-bromopentanoate.

The mixture is heated for 6 hours under reflux, then filtered after cooling. The precipitate is dissolved in a minimum amount of water and the solution obtained is acidified with concentrated hydrochloric acid. The desired product precipitates (10.2 g.). It can be crystallized in methanol by adding diethyl oxide. White crystals are produced which melt at 160°C.

| Analysis: | N | S |
|---|---|---|
| Calculated, % | 5.16 | 11.85 |
| Found, % | 5.46 | 12.03 |

EXAMPLE 10

2-(5-methoxycarbonyl pentylthio)ethylamine hydrochloride (Method I)

$$CH_3OCO(CH_2)_5-S-CH_2CH_2NH_2 \cdot HCl$$

There are added successively, to a solution of 2.6 g of potassium in 100 cc of methanol, 4.5 g of β-mercaptoethylamine hydrochloride, then slowly 8.2 g of methyl ω-bromohexanoate.

The mixture is heated for 3 hours under reflux. After cooling, it is acidified with gaseous hydrochloric acid and filtered. The filtrate is evaporated to dryness and the oily residue (8 g) crystallizes rapidly. The product melts at 80°C after crystallization in a mixture of methanol and diisopropyl oxide.

| Analysis: | Cl |
|---|---|
| Calculated, % | 14.70 |
| Found, % | 14.78 |

EXAMPLE 11

3-(2-p-toluenesulfonamidoethylthio) alanine (Method I)

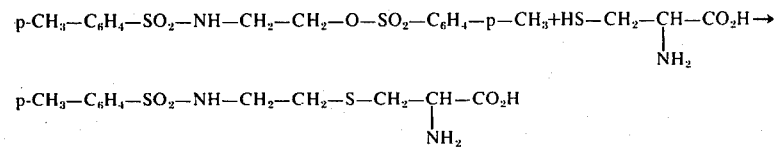

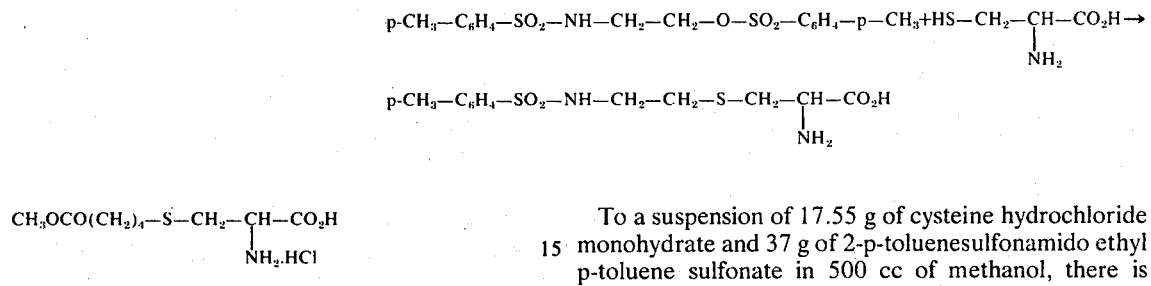

To a suspension of 17.55 g of cysteine hydrochloride monohydrate and 37 g of 2-p-toluenesulfonamido ethyl p-toluene sulfonate in 500 cc of methanol, there is added, during a 1 hour period, at 50°C. a solution of 19.6 g of potassium at 85% in 500 cc of methanol.

The potassium chloride and potassium p-toluene sulfonate are removed by filtration. The mother liquor is evaporated to dryness, leaving an oil which is mixed with water and acidified with acetic acid. The product precipitates and is crystallized in water. Yield is 29 g. Fusion point is 215°C.

EXAMPLE 12

2-methylthioethylammonium phenylacetate (Method I)

$$CH_3S-CH_2-CH_2-N^+H_3O^-{}_2C-CH_2-C_6H_5$$

There are added, progressively and with intense agitation, 41 g of 2-bromo ethylamine hydrobromide to a solution of sodium methanethiolate in ethanol (starting with 9.6 g of methane thiol and 9.2 g sodium).

The mixture is agitated for 1 hour at ambient temperature, then heated under reflux for 30 minutes. After cooling, the mixture is diluted with 200 cc of ether and then filtered to remove therefrom the mineral salts. The filtrate is concentrated and the resulting oily residue is fractionated. The fraction distilling at 42°C under 16 mm Hg, is recovered and yields 13.6 g (75%) of 2-methylthioethylanine which are added, in a solution of ether (300 cc), to a solution of phenyl-acetic acid (0.15 mol) in the same solvent. The salt formed crystallizes, in proportion to the addition, in the form of white needles (33.5 g) which are purified by crystallization in ethyl acetate. Yield = 92%. Fusion point: 92°–94°C.

| Analysis: | N | S |
|---|---|---|
| Calculated, % | 6.16 | 14.10 |
| Found, % | 6.11 | 14.01 |

EXAMPLE 13

3-(9,11 dihydroxy 10,10-dimethyl 4,8-dioxo 3,7-diaza undecylthio)alanine- (Method IV)

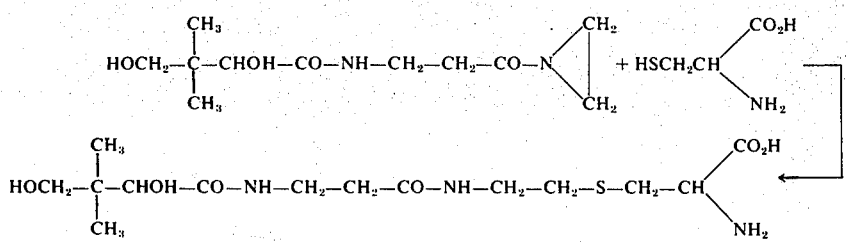

15

10 g of calcium pantothenate are dissolved in 10 cc of water. To this solution are added, in succession, 2.66 g of oxalic acid in a minimum of water and 10 cc of triethylamine. The calcium oxalate formed is removed by filtration. There is obtained triethylamine pantothenate in the form of an oil by concentrating the filtrate to dryness.

This salt is dissolved in 25 cc of anhydrous dimethyl formamide and the solution is cooled to −5°C. Then dropwise, while maintaining the temperature at −5°C, there is added a solution of 4.1 g of ethyl chloroformate.

The mixture is added dropwise to a solution of 25 g ethyleneimine and 5 g of triethylamine in 50 cc of ethyl acetate while maintaining the temperature at −5°C. The mixture is agitated for 20 minutes at −5°C.

During a period of about 15 minutes, there is added a filtered solution of 6.6 g of cysteine hydrochloride and 4.2 g of triethylamine in 20 cc of dimethyl formamide. After 30 minutes at 0°C, the solution is filtered and the filtrate is evaporated to dryness under a vacuum. The oily residue is dissolved in ethyl ether and after standing, crystallizes in the form of a white hygroscopic product, the fusion point of which is 75°–80°C. Yield = 75%.

The proportion of carboxylic acid and amine functions correspond to theory.

EXAMPLE 14

2-amino-4-thia nonadioic acid (Method II)

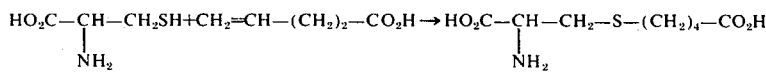

10 g of allylacetic acid are added dropwise to 15.75 g of cysteine hydrochloride. Under intense agitation, there are added 10 mg of benzoyl peroxide. The mixture becomes heated and liquifies and is maintained for 1 hour at 80°C. After cooling, it is dissolved in 50 cc of 2 N soda. The precipitate that forms is filtered and washed with water. Yield: 16.5 g. After crystallization is dilute hydrochloric acid, the product melts at 230°C with decomposition.

The proportion of carboxylic acid function corresponds to theory.

EXAMPLE 15

Bis[2-(2,2-dimethoxyethylthio)ethylamine]oxalate (Method I)

16

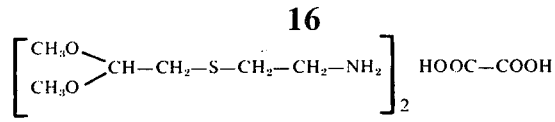

To a solution of 4.6 g of sodium in 150 cc of ethanol, there are added 11.35 g of β-mercaptoethylamine hydrochloride, the, dropwise 16.9 g of the bromide of 2,2'-dimethoxyethyl bromoacetaldehyde dimethylacetal.

The mixture is heated for 2 hours under reflux. The mineral salts are filtered after cooling and the mother liquor is concentrated. The oily residue is distilled in 17 mm Hg at 125°–130°C. Yield = 74%.

The 12.2 g of 2-(2,2-dimethoxyethylthio)ethylamine obtained above are dissolved in 50 cc of ethanol and added to a solution of 4.65 g of the dihydrate of oxalic acid. The salt formed cyrstallizes by addition of ethyl ether, after cooling. By crystallization in 2-propanol and ethyl ether, white crystals are obtained. Fusion point: 170°–172°C. Weight: 28.6 g

| Analysis: | N | S |
|---|---|---|
| Theory, % | 6.66 | 15.25 |
| Found, % | 6.58 | 15.18 |

EXAMPLE 16

2-(2-p-methoxyphenyl 2-propylthio)ethylamine hydrochloride (Method III)

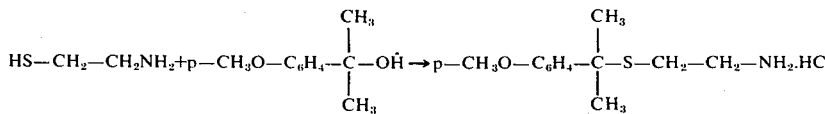

To a solution of 11.25 g of β-aminoethylthio in 50 cc acetic acid there are added successively 15.42 g of p-methoxy phenyl dimethyl carbinol and a solution of boron trifluoride in acetic acid. The mixture is heated 30 minutes at 60°C, then cooled. This solution is added dropwise to a 10% solution of sodium acetate, which is extracted three times with ethyl ether and dried over sodium sulfate. By bubbling gaseous hydrochloric acid in the etherified solution, the product is produced as a white precipitate. Fusion point with decomposition: 172°–174°C. Yield: 62%.

| Analysis: | C | H | N |
|---|---|---|---|
| Theory, % | 55.05 | 7.70 | 5.35 |
| Found, % | 54.98 | 7.85 | 5.21 |

EXAMPLE 17

2-acetamido 3-(2,4-dichlorobenzylthio(propionic acid (Method I and VII)

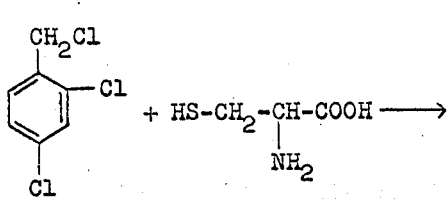

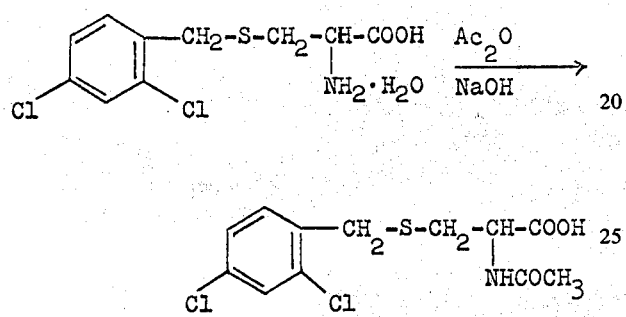

To a solution of 6.9 g of sodium in 400 cc of absolute ethanol, there are added, successively, 15.75 g of cysteine hydrochloride and 19.54 g of 2,4-dichloro benzyl chloride.

Then the mixture is heated at 50°C for a period of one hour. By adding 600 cc of water and 30 cc of acetic acid, the product crystallizes in the form of needles. Fusion point 205°–210°C.

24.5 g of this product, 2-amino 3-(2,4-dichlorobenzylthio)propionic acid, are acetylated in accordance with the conventional Schatten-Baumann reaction. There is obtained a precipitate which is crystallized in 40% ethanol, weight: 23.85 g. Fusion point: 134°–135°C.

| Analysis: | C | H | N |
|---|---|---|---|
| Theory, % | 44.73 | 4.06 | 4.34 |
| Found, % | 44.78 | 4.17 | 4.35 |

EXAMPLE 18

3-[Bis-(p-methoxy phenyl) 3-methylthio]alanine (Method III)

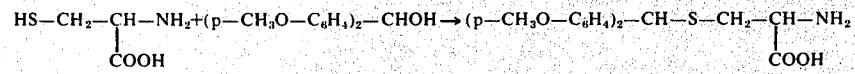

A solution of 17.56 g of cysteine hydrochloride monohydrate in 85 cc of acetic acid is heated with agitation at 60°C. Then there is added, sucessively, 24.4 g of bis-(p-methoxyphenyl)carbinol and 20.7 g of boron trifluoride in acetic acid. The mixture is heated at 80°C for a period of 15 minutes, then cooled to 10°C. Then, by adding a solution of 48 g of sodium acetate in 50 cc of water and 150 cc of ethanol, the product precipitates. After crystallization in a mixture of water and dimethylformamide, there are obtained white crystals, the fusion point of which is 209°–211°C. Yield: 85%.

| Analysis: | C | H | N |
|---|---|---|---|
| Theory, % | 62.22 | 6.09 | 4.03 |
| Found, % | 62.38 | 6.15 | 4.22 |

EXAMPLE 19

2-allylthioethylammonium malate (Method I)

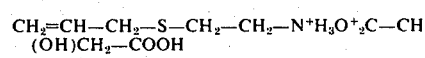

24.2 g of allyl bromide are added dropwise to a solution of 22.7 g of β-aminoethylthio in 150 cc of ethanol containing 9.2 g of metallic sodium. The mixture is heated under reflux for 1 hour. The resulting oil phase is decanted and is dissolved by adding ether thereto in order to eliminate by filtration the mineral salts. The filtrate is concentrated under vacuum, leaving an oily residue. Weight: 38.1 g. The oily residue is dissolved in 100 cc of absolute ethanol and 43.5 g of malic acid are added with agitation in small portions. By adding ether, the product forms as a white precipitate which, after crystallization in 2-propaol, melts at 94°C. Yield: 65%.

| Analysis: | N | S | C | H |
|---|---|---|---|---|
| Theory, % | 5.57 | 12.76 | 43.01 | 6.81 |
| Found, % | 5.56 | 12.66 | 43.04 | 6.90 |

EXAMPLE 20

2-amino 4-β-aminoethylthio butyric acid (Method I)

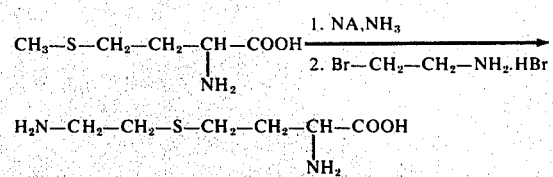

There are added, in small amounts, 21.52 g of sodium to a suspension of 40 g of methionine in 1.5 l of liquid ammonia. After the addition, the mixture is maintained under agitation for 4 hours. There is then added to the mixture sufficient ammonium chloride to decolorize the solution. The ammonia is evaporated overnight at ambient temperature and the white residue is dissolved in 200 cc of water. There is added, over a 2-hour period, a solution of 55 g of 2-bromo ethylamine hydrobromide in 300 cc of water. The mixture is agitated for 3 hours at 20°C and then for 3 hours at 50°C. The reaction product is then treated with DOWEX Resin 50 W, and then eluted by means of an ammoniacal solution. The eluate is concentrated under vacuum. The solid residue is admixed with 75 cc of water, neutralized with 52 cc of 6N hydrochloric acid and treated with animal charcoal. There is obtained after filtration a colorless solution which is then concentrated under vacuum. The solid residue is crystallized in a mixture of water, methanol, acetone and is in the form of white crystals (38 g) melting at 216°–217°C.

| Analysis - $C_6H_{15}ClN_2O_2S$ | | | | |
|---|---|---|---|---|
| | C | H | N | HCl |
| Calculated, % | 33.66 | 7.03 | 13.05 | 17.03 |
| Found, % | 33.61 | 7.18 | 13.08 | 17.08 |

EXAMPLE 21

S-β-aminoethyl mercaptobutyric acid (Method I)

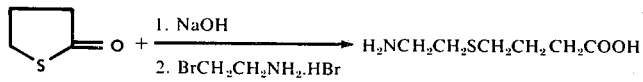

A solution of 51 g of 2-thiolannone in 50 cc of methanol is added to a solution of 150 cc of 10 N soda, 400 cc of water and 500 cc of methanol. In the resulting solution, there is introduced, in several portions, 103 g of β-bromoethylamine hydrobromide. The mixture is heated under reflux for 3 hours. The solution is treated with an ion exchange resin in hydrogen form, in accordance with conventional procedures. The concentrated eluate provides a solid residue which is washed in ethanol and filtered. Yield: 62.5 g. Fusion point: 171°C.

The proportion of acid and amine functions conform to theory.

EXAMPLE 22

S-β-ureidoethylmercaptoacetic acid (Methods I and VIII)

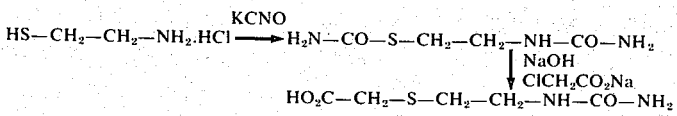

To a solution of 34.1 g of β-mercaptoethylamine hydrochloride in 200 cc of water there is added a solution of 24.3 g of potassium cyanate in 80 cc of water, then 36 g of sodium monochloroacetate in 200 cc of water. The solution is heated at 50°C for 2 hours while maintaining the pH at 6 by the addition of 2N soda. The mixture is then acidified, concentrated to dryness and washed with a mixture of water and ethanol. After filtration, there is produced 42 g of the product which melts at 135°C.

| Analysis: | C | H | N | S |
|---|---|---|---|---|
| Calculated, % | 33.69 | 5.65 | 15.72 | 17.99 |
| Found, % | 33.79 | 5.67 | 15.62 | 18.07 |

EXAMPLE 23

2-methoxycarbonylmethylthioethylamine hydrochloride (Method V)

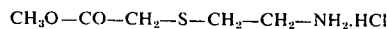

13.5 g of S-(β-aminoethyl)mercaptoacetic acid and 10.8 g of 2,2-dimethoxy propane are added, successively, to a solution of 7.3 g of gaseous hydrochloric acid in 20 cc of methanol. The solution is permitted to stand for 12 hours at ambient temperature. The flasks formed (17.5 g) are filtered and washed with ethyl acetate. Fusion point = 100°C.

| Analysis: | Cl |
|---|---|
| Calculated, % | 19.1 |
| Found, % | 19.2 |

EXAMPLE 24

N-(2-benzylthioethyl)2,4-dihydroxy 3,3-dimethyl butyramide (Method VII)

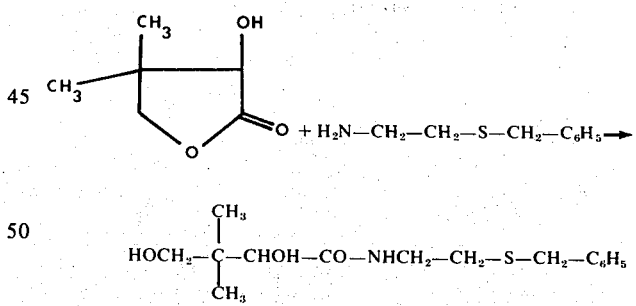

13 g of pantolacetone with a few drops of a methanol solution of sodium methylate are added to a solution of 16.7 g 2-benzylthio ethylamine in 50 cc of ethanol. The mixture is heated for 6 hours at 60°–65°C.

After cooling, the product is crystallized by addition of diethyl oxide. White crystals (23.8 g) melt at 70°C.

EXAMPLE 25

2-β-hydroxyethylthioethylamine hydrochloride (Method IV)

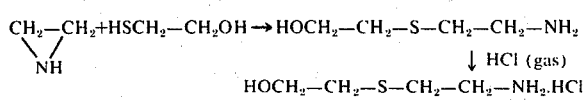

There are added in 1 hour, 39 g of 2-mercapto ethanol in 50 cc of ethanol to a solution of 21.5 g of ethyleneimine in 100 cc of ethanol. The mixture is maintained for 10 hours at 40°C and then concentrated to dryness. The oily residue (56 g) is fractionated under vacuum (1.5 mm Hg) and the fraction distilling at 113°–116°C (48 g) is recovered.

By the action of gaseous hydrochloric acid on an ethanol solution of the distilled amine, there is obtained the hydrochloride in the form of crystals (59 g) which melt at 45°–48°C.

| Analysis: | HCl |
|---|---|
| Calculated, % | 23.15 |
| Found, % | 23.10 |

EXAMPLE 26

3,3'-(2',2-sulfonyl diethylthio)dialanine and the N,N'-diacetyl derivative thereof. (Method II and VII)

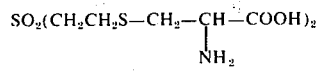

To a solution of 70.2 g of cysteine hydrochloride monohydrate in 300 cc of water, there is added, successively, 53 cc of 8 N soda, 0.5 cc of concentrated ammonia and after 30 minutes, a solution of 23.6 g of divinyl sulfone in 300 cc of water. After two hours under agitation, the reaction mixture is filtered and the precipitate (67 g) is washed with water and with ethanol.

| Analysis: | C | H | N |
|---|---|---|---|
| Calculated, % | 33.31 | 5.59 | 7.77 |
| Found, % | 32.99 | 5.56 | 7.72 |

21.6 g of the precipitate obtained above are dissolved in 30 cc of water and 15 cc of 8N soda. To this solution, there is added, successively, 60 cc of acetic anhydride and 112.8 cc of 8N soda.

Agitation of the mixture is continued for some time and it is acidified with 147.6 cc of 10N hydrochloric acid. The precipitate formed in filtered and washed with water. Yield: 21.42 g. Fusion point: 196°C.

| Analysis: | C | H | N |
|---|---|---|---|
| Calculated, % | 37.82 | 5.44 | 6.30 |
| Found, % | 37.38 | 5.43 | 6.35 |

EXAMPLES OF COMPOSITIONS AND THEIR USE IN ACCORDANCE WITH THIS INVENTION

EXAMPLES 27–34

The following composition is prepared and is usefully employed to reduce excessive secretion of sebum on the scalp. It is orally administered in the form of drops.

| | |
|---|---|
| 3-allyl thio alanine hydrochloride | 1 g |
| Glycerine | 40 g |
| Ethyl alcohol | 30 g |
| Water, q.s.p. | 100 g |
| Lemon tincture (q.s.p. impart a pleasing aroma) | |

The oral administration of this composition at the rate of 10 drops each day for 15 days by a person having greasy hair due to excessive secretion of sebum substantially improves the condition of the scalp and the appearance of the hair.

Essentially similar effective results are obtained when the 3-allyl thio alanine hydrochloride is replaced with the following compounds: 3-(β-hydroxyethyl thio) alanine, 2-amino, 4-thia dodecanoic acid, 2-(2-naphthyl thio) ethyl ammonium disuccinate, 2-(pyridyl-2-methyl thio) ethylamine dihydrochloride, 2-cetylthio ethylamine hydrochloride, 2-(3,4-dimethoxy benzylthio) ethylammonium malate and 2-amino 4-tetradecylthio butyric acid.

EXAMPLES 35–41

The following composition is prepared:

| | |
|---|---|
| 3-methylthio alanine hydrochloride | 50 mg |
| Glucose | 300 mg |
| Water, q.s.p. | 5 ml |
| Orange juice (q.s.p. to impart a pleasant aroma) | |

The oral administration of this composition, at the rate of 2 ampoules each day for 15 days by a person having greasy hair due to excessive secretion of sebum substantially improves the condition of the scalp and the appearance of the hair.

Essentially similar effective results are achieved by replacing the 3-methylthio alanine hydrochloride with the following compounds: 3-(2,4-dichlorobenzylthio)alanine, 3,3'-(2-butene 1,4 diyldithio)dialanine, 2-(2,2-dimethoxy ethylthio)ethylamine hydrochloride, S-(3-aminopropyl)mercapto acetic acid, 2-(2,4-dichlorocetylthio)ethylamine and 5-dodecanamido 3-thia hexanedioic acid.

EXAMPLE 42–48

Lozenges for oral consumption having the following composition are prepared:

| | |
|---|---|
| 3-(β-ureidoethylthio)alanine | 20 mg |
| Lactose | 300 mg |
| Powdered gum arabic | 100 mg |
| Simple syrup, q.s.p. | 500 mg |

These lozenges, taken at a rate of 15 each day, by a person having greasy hair and scalp due to excessive secretion of sebum substantially improves the condition of the scalp and the appearance of the hair by reducing excessive secretion of sebum.

Essentially similar effective results are achieved by replacing the 3-(β-ureidoethylthio)alanine by the following compounds: 3-octylthio alanine, 2-(3,4 methylenedioxybenzylthio)ethylamine hydrochloride, 3-(2-pyridyl N-oxide methylthio)alanine, o-fluorobenzylthioethylamine hydrochloride, 2-amino 4-(o-chlorobenzylthio)methyl butyrate hydrochloride, and 6-amino 3-thia dimethyl heptanedioate hydrochloride.

EXAMPLES 49–53

Chewable pellets having the following composition are prepared:

| | |
|---|---|
| 3-(2-pyridyl methylthio)alanine | 2.5 g |
| Sucrose | 200 g |
| Lemon syrup | 50 g |

These pellets, administered at the rate of a coffee spoonful twice a day to a person having greasy hair and scalp due to excessive secretion of sebum substantially reduces excessive secretion of sebum and thereby significantly improves the condition of the scalp and the appearance of the hair.

Essentially similar effective results are achieved by replacing 3-(2-pyridyl methylthio)alanine by the following compounds: 6-amino 3-thia heptanedioic acid, 2-(undecenyl thio)ethylamine, 3-methylthio 2-propionamide dimethyl amino ethyl propionate and 3-benzylthio 2-butyramido propionic acid.

EXAMPLES 54–56

Tablets having the following compositions are prepared:

| | |
|---|---|
| 5-p-toluenesulfonamido 3-thia hexane dioicacid | 10 mg |
| Lactose | 150 mg |
| Gum arabic | 100 mg |
| Starch, q.s.p. | 500 mg |

These tablets taken at a rate of 10 each day for 20 days by a person having greasy hair and scalp because of excessive secretion of sebum effectively reduces excessive sebum secretion and significantly improves the appearance of the hair and scalp condition.

Essentially similar effective results are achieved when 5-p-toluenesulfonamido 3-thia hexane dioic acid is replaced by the following compounds: 2,4-dichloro 2-benzyl thio ethylamine aspartate and N-[2-(3,5 dichloro benzylthio) ethyl] trifluoro acetamide.

Table I below lists active compounds which are cysteine derivatives and which are usefully employed in the present invention. Table I identifies the general method by which the active compounds are prepared in accordance with methods I–VIII, above, as well as representative compositions in which they are included for oral administration to humans having a scalp characterized by excessive secretion of sebum, to reduce said excessive secretion so as to improve the condition of the scalp and to improve the appearance of the hair.

TABLE I

| NO. | Active Compound | Method of Preparation | Form of Composition | Amount in Composition |
|---|---|---|---|---|
| 1 | 3-methylthio alanine | I | Drops as in Ex. 27–34 | .75 g |
| 2 | 3-methylthio alanine hydrochloride | I | " | .75 |
| 3 | 3-isopropylthio alanine | I or III | " | .75 |
| 4 | 3-n-octylthio alanine | I | " | .75 |
| 5 | 3-(2-ethyl hexylthio)alanine | I | " | .75 |
| 6 | 3-dodecylthio alanine | I | " | 1.00 |
| 7 | 3-hexadecylthio alanine | I | " | 1.00 |
| 8 | 3-octadecylthio alanine | I | " | 1.00 |
| 9 | 3-(9-octadecene-ylthio) alanine | I | " | 1.00 |
| 10 | 3-allylthio alanine | I | " | 1.00 |
| 11 | 3-allylthio alanine hydrochloride | I | " | 1.25 |
| 12 | 3-(2-butene-ylthio)alanine | I | " | 1.25 |
| 13 | 1,2-dichloro 3-vinylthio alanine | I | " | 1.25 |
| 14 | 3-(2-propyne-ylthio)alanine | I | " | 1.25 |
| 15 | 3-t-butylthio alanine | III | " | 1.25 |
| 16 | 3,3'-(2-butene 1,4-diyl-dithio)dialanine | I | " | 1.50 |
| 17 | 3-β-hydroxyethylthio alanine | I or IV(alternative) | " | 1.50 |
| 18 | 3-(2,3-dihydroxy propylthio)alanine | IV(alternative) | Drops as in Ex. 27–34 | 1.50 g |
| 19 | 3-(2-hydroxy propylthio) alanine | IV(alternative) | " | 1.50 |
| 20 | 3-(2,2-(dimethoxy ethylthio)alanine | I | " | 1.50 |
| 21 | 3-(3,3-diethoxy propylthio)alanine | I or II | " | 2.00 |
| 22 | 3-(1,2-propylenedioxy ethylthio)alanine | I | " | 2.00 |
| 23 | 3-(2,2-ethylenedioxy propylthio)alanine | I or II | " | 2.00 |
| 24 | 3-β-ureidoethylthio alanine | I | " | 2.00 |
| 25 | 3-β-acetamidoethylthio alanine | I or IV | " | 2.00 |
| 26 | 2-β-p-toluenesulfonamido 3-ethylthio alanine | I or IV | " | 2.50 |
| 27 | 3-β-phenylacetamidoethylthio alanine | I | " | 2.50 |
| 28 | 3-β-aminoethylthio alanine | I or IV | " | 2.50 |
| 29 | 3-β-nicotinamidoethylthio alanine | I or IV | " | 3.00 |
| 30 | 3-[2-(2,4-dihydroxy 3,3-dimethyl butyramido) ethylthio] alanine | VII | " | 3.00 |
| 31 | 3-[9,11-dihydroxy 10,10-dimethyl 4,8-dioxo 3,7-diaza undecylthio] alanine | IV | " | 3.00 |

TABLE I-continued

| NO. | Active Compound | Method of Preparation | Form of Composition | Amount in Composition |
|---|---|---|---|---|
| 32 | 3,3'-thio dialanine | II | " | 3.00 |
| 33 | 3-(ω-amino ω-carboxypropylthio) alanine | I or II | " | 3.00 |
| 34 | S-(3-alanyl) N-acetyl cysteine | II | Ampoules as in Ex. 35–41 | 50 mg |
| 35 | 3-(2-naphthyl thio) alanine | I or II | " | 50 mg |
| 36 | S,S'-[2,3-dihydroxy 1,4-butanediyl] bis cysteine | I | " | 50 mg |
| 37 | 3-(2-thenylthio) alanine | I | " | 50 mg |
| 38 | 3-o-chlorobenzylthio alanine | I | " | 50 mg |
| 39 | 3-p-chlorobenzylthio alanine | I | " | 50 mg |
| 40 | 3-furfurylthio alanine | I | " | 50 mg |
| 41 | 3-tetrahydrofurfurylthio alanine | I | " | 50 mg |
| 42 | 3-(2-pyridyl methylthio) alanine | I | " | 50 mg |
| 43 | 3-β-phenylethylthio alanine | I or II | " | 50 mg |
| 44 | 3-(2-pyridyl thio) alanine | I | " | 50 mg |
| 45 | 3-diphenylmethylthio alanine | III (and I) | " | 50 mg |
| 46 | 3-(2-pyridyl ethylthio) alanine | II or I | " | 50 mg |
| 47 | 3-(2,4-dichloro benzylthio) alanine | I | " | 50 mg |
| 48 | 3-(3,4-dichloro benzylthio) alanine | I | " | 50 mg |
| 49 | 3-(3,5-dichloro benzylthio) alanine | I | " | 50 mg |
| 50 | 3-(2,6-dichloro benzylthio) alanine | I | " | 50 mg |
| 51 | 3-o-methoxybenzylthio alanine | I | Ampoules as in Ex. 35–41 | 50 mg |
| 52 | 3-p-butoxybenzylthio alanine | I | " | 50 mg |
| 53 | 3-p-methoxybenzylthio alanine | I | " | 50 mg |
| 54 | 3-p-bromobenzylthio alanine | I | " | 50 mg |
| 55 | 3-m-fluorobenzylthio alanine | I | " | 50 mg |
| 56 | 3-(3,4-dimethoxy benzylthio)alanine | I | " | 50 mg |
| 57 | 3-(3,4-methylenedioxy benzylthio)alanine | I | " | 50 mg |
| 58 | 3-p-fluorobenzylthio alanine | I | " | 50 mg |
| 59 | 3-(3,4,5-trimethoxy benzylthio)alanine | I | " | 50 mg |
| 60 | 3-(2-pyridyl N-oxide methylthio)alanine | I | " | 50 mg |
| 61 | 3-o-methylbenzylthio alanine | I | " | 50 mg |
| 62 | 3-p-methylbenzylthio alanine | I | " | 50 mg |
| 63 | 3-(4-t-butyl benzylthio)alanine | I | " | 50 mg |
| 64 | 3-o-fluorobenzylthio alanine | I | " | 50 mg |
| 65 | 3-(4-isopropyl benzylthio) alanine | I | " | 50 mg |
| 66 | 3-(2,4-dimethyl benzylthio) alanine | I | Lozenges as in Ex. 42–48 | 10 mg |
| 67 | 3-p-trifluoromethyl benzylthio alanine | I | " | 10 mg |
| 68 | 3-o-trifluoromethyl benzylthio alanine | I | Lozenges as in Ex. 42–48 | 10.00 mg |
| 69 | 3-p-acetamidobenzylthio alanine | I | " | 10.00 |
| 70 | 3-p-dimethylamino-benzylthio alanine | I | " | 10.00 |
| 71 | 3-p-phenoxybenzylthio alanine | I | " | 15.00 |
| 72 | 3-p-phenylbenzylthio alanine | I | " | 15.00 |
| 73 | 3-(4-methylthio benzylthio)alanine | I | " | 15.00 |
| 74 | 3-(4-propylsulfonyl benzylthio)alanine | I | " | 15.00 |
| 75 | 3-(4-butylsulfonyl benzylthio) alanine | I | " | 15.00 |
| 76 | 3-(2-methylthio benzylthio)alanine | I | " | 15.00 |
| 77 | 3-benzylthio alanine | I | " | 17.50 |
| 78 | 2-amino 3-benzylthio propionamide hydrochloride | VI | " | 17.50 |
| 79 | 3-benzylthio 2-nicotinamido propionate of 2-hydroxy 2-propyl | V or VII | " | 17.50 |
| 80 | 3-benzylthio 2-nicotinamido propionic acid | VII | " | 17.50 |
| 81 | 3-ethoxycarbonyl methylthio alaninate of ethyl | V | " | 17.50 |
| 82 | 5-p-toluene sulfonamido 3-thia hexanedioic acid | VII | " | 8.00 |
| 83 | 5-p-acetamidobenzene sulfonamido 3-thia hexanedioic acid | VII | " | 8.00 |
| 84 | 2-propionamido 3-thia hexanedioic acid | VII | Lozenges as in Ex. 42–48 | 8.00 |
| 85 | 2-p-acetamidobenzamido 3-benzylthio propionic acid | VII | " | 8.00 |
| 86 | 2-methanesulfonamido 3-dodecylthio | VII | " | 8.00 |
| 87 | 5-benzamido 3-thia hexanedioic acid | VII | " | 8.00 |
| 88 | 2-glutamino 3-methylthio propionic acid | VII | " | 8.00 |
| 89 | 5-ureido 3-thia hexanedioic acid | VIII | " | 8.00 |
| 90 | N-(2-amino 3-benzylthio propionyl) glucosamine hydrochloride | VI | " | 8.00 |
| 91 | 2-formamido 4-thia heptanedioic acid | VII | " | 8.00 |
| 92 | 3-benzylthio 2-(9-octadecene amido) propionic acid | VII | " | 8.00 |
| 93 | 2-amino 3-benzylthio propionhydroxamic acid | VI | " | 15.0 |
| 94 | 2-acetamido 3-benzylthio propionhydrazide | VI | " | 15.0 |
| 95 | 2-propionamido 3-benzylthio propionhydroxamic acid | VI | " | 15.0 |
| 96 | 3-p-ethoxy benzylthio alanine | I | " | 15.0 |
| 97 | bis-(p-methoxyphenyl)-3-methylthio alanine | I or III | " | 15.0 |
| 98 | 3-(2-p-methoxyphenyl 2-propyl thio) alanine | I or III | Chewable pellets as in Ex. 49–53 | 1.90 g |

TABLE I-continued

| NO. | Active Compound | Method of Preparation | Form of Composition | Amount in Composition |
|---|---|---|---|---|
| 99 | 3-(2-naphthyl methylthio)alanine | I | " | 1.90 g |
| 100 | 3-phenylthio alanine | I(alternative) or II | " | 1.90 g |
| 101 | 3-o, m or p-chlorophenylthio alanine | I(alternative) or II | " | 1.90 g |
| 102 | 3-p-fluorophenylthio alanine | I(alternative) or II | " | 1.90 g |
| 103 | 3-o or p-methoxyphenylthio alanine | I(alternative) or II | " | 1.90 g |
| 104 | 3-benzylthio valine | II | " | 2.5 g |
| 105 | 2-amino 4-benzylthio butyric acid | I | " | 2.5 g |
| 106 | 3-carbamyl methylthio alanine | I | " | 2.5 g |
| 107 | 3-γ-aminopropylthio alanine | I | " | 2.5 g |
| 108 | 3-o-aminophenylthio alanine | I | " | 2.5 g |
| 109 | 3-(2-carboxy ethylthio)alanine | II or I | " | 2.5 g |
| 110 | 3-β-butoxy carbonyl ethylthio alanine | II | " | 3.75 g |
| 111 | 3-propoxy carbonylmethylthio alanine | V | " | 3.75 g |
| 112 | 3-ω-methoxycarbonyl butylthio alanine | I | " | 3.75 g |
| 113 | 3-ω-methoxy carbonyl pentylthio alanine | I | " | 3.75 g |
| 114 | 3-(3-carboxy propylthio)alanine | I | " | 3.75 g |
| 115 | 2-amino 4-thia nonanedioic acid | II | Chewable pellets as in Ex. 49–53 | 5.0 g |
| 116 | 2-amino 4-thia decanedioic acid | I | " | 5.0 g |
| 117 | 2-amino 4-thia dodecanedioic acid | I | " | 5.0 g |
| 118 | 3-carboxymethylthio alanine | I | " | 5.0 g |
| 119 | N-(2-acetamido 3-benzylthio propionyl) glucosamine | VI | " | 5.0 g |
| 120 | 3-benzylthio 2-(10-undecene-amido) propionic acid | VII | " | 5.0 g |
| 121 | 3-benzylthio 2-octadecanamido propionic acid | VII | " | 6.25 g |
| 122 | 3-carbamylthio alanine | VIII | " | 6.25 g |
| 123 | 3-methylthio 2-propionamido propionate of dimethylaminoethyl | V | " | 6.25 g |
| 124 | 2-acetamido 3-benzylthio propionate of diethylaminoethyl | V | " | 6.25 g |
| 125 | 3-benzylthio 2-propionamido propionate of 1-butoxy 2-propanol | V | " | 7.50 g |
| 126 | 5-amino 3-thia hexanedioate of di-(β-piperidinoethyl) hydrochloride | V | " | 7.50 g |
| 127 | 3,3-(2,2-sulfonyl diethylthio)dialanine | II | " | 7.50 g |
| 128 | 3-o-nitrophenylthio alanine | I | " | 7.50 g |
| 129 | 3-β-piperidinocarbonyl ethylthio alanine | I or II | Tablets as in Ex. 54–56 | 6 mg |
| 130 | 2-acetamido 3-pyrrolidinocarbonylmethyl-thio propionic acid | I | " | 6 mg |
| 131 | 2-amino 4-ortho-chlorobenzylthio butyrate of methyl hydrochloride | I | " | 6 mg |
| 132 | 2-amino 4-β-amino ethylthio butyric acid hydrochloride | I | " | 6 mg |
| 133 | 2-propionamido 4-tetradecylthio butyric acid | VII | " | 6 mg |
| 134 | 2-amino 4-tetradecylthio butyric acid | I | " | 6 mg |
| 135 | 6-amino 3-thia heptanedioic acid | I | " | 6 mg |
| 136 | S,S'-(2 butene 1,4-diyl)bis-homocysteine | I | " | 6 mg |
| 137 | N-formyl S-methyl penicillamine | I or II | " | 6 mg |
| 138 | 2-amino 4-thia heptanedioic acid | II or I | " | 7,5 mg |
| 139 | S-carboxymethyl cysteinate of methyl | VII | " | 7,5 mg |
| 140 | 5-nicotinamido 3-thia hexanedioic acid | VII | " | 7,5 mg |
| 141 | 5-p-acetamidobenzamido 3-thia hexanedioic acid | VII | " | 7,5 mg |
| 142 | 5-p-butoxybenzamido 3-thia hexanedioic acid | VII | " | 7,5 mg |
| 143 | 5-dodecanamido 3-thia hexanedioic acid | VII | " | 7,5 mg |
| 144 | 6-amino 3-thia heptanedioate of dimethyl | V | Tablets as in Ex. 54–56 | 7.50 mg |
| 145 | 5-p-methoxybenzamido 3-thia hexanedioic acid | VII | " | 7.50 mg |
| 146 | 2-acetamido 4-thia nonanedioic acid | VII | " | 7.50 mg |
| 147 | 3-benzylthio 2-butyramido propionic acid | VII | " | 7.50 mg |
| 148 | 3-benzylthio 2-propionamido propionic acid | VII | " | 7.50 mg |
| 149 | 3-benzylthio 2-methanesulfonamido propionic acid | VII | " | 7.50 mg |
| 150 | 3-benzylthio 2-ethanesulfonamido propionic acid | VII | " | 10.0 mg |
| 151 | 3-benzylthio 2-propanesulfonamido propionic acid | VII | " | 10.0 mg |
| 152 | 3-benzylthio 2-butanesulfonamido propionic acid | VII | " | 10.0 mg |
| 153 | 2-acetamido 3-benzylthio propionic acid | VII | " | 10.0 mg |
| 154 | 2-amino 3-benzhydryl propionate of methyl hydrochloride | V | " | 10.0 mg |
| 155 | 5-acetamido 3-thia hexanedioic acid | VII | " | 10.0 mg |
| 156 | S-(carboxymethyl) cysteinate of butyl | I | " | 12.5 mg |
| 157 | S-(ethoxy carbonyl methyl) cysteine | I and V | " | 12.5 mg |
| 158 | S-(propoxy carbonyl methyl) cysteine | I and V | " | 12.5 mg |
| 159 | S-(butoxy carbonyl methyl) cysteine | I and V | Tablets as in Ex. 54–56 | 12.5 mg |
| 160 | S-(methoxy carbonyl ethyl) cysteine | II | " | 15.0 mg |
| 161 | S-(methoxy carbonyl propyl) cysteine | I and V | " | 15.0 mg |
| 162 | S-(methoxy carbonyl butyl) cysteine | I and V | " | 15.0 mg |
| 163 | 3-(1-naphthyl 2-methylthio) alanine | I | " | 15.0 mg |

Table II, below, lists active compounds which are cysteamine derivatives and which are usefully employed in the present invention. Table II identifies the general method by which the active compounds are prepared in accordance with Methods I–VIII disclosed hereinbefore, as well as representative compositions in which they are included for oral administration to humans having a scalp characterized by excessive secretion of sebum to reduce said excessive secretion so as to improve the condition of the scalp and to improve the appearance of the hair.

TABLE II

| No. | Active Compound | Method of Preparation | Form of Composition | Amount in Composition |
|---|---|---|---|---|
| 1 | 2-methylthio ethylamine (cinnamate) | I or IV | Drops as in Ex. 27–54 | 0.75 g |
| 2 | 2-methyl thio ethylurea | I or VIII | " | 0.75 g |
| 3 | N-(2-methylthio ethyl) p-acetamido benzamide | VII, IV or I | " | 0.75 g |
| 4 | N-(2-methylthio ethyl)p-acetamido benzenesulfonamide | VII, IV or I | " | 0.75 g |
| 5 | N-(2-propylthioethyl)-p-methoxy benzamide | VII, IV or I | " | 0.75 g |
| 6 | N-(butylthio ethyl) nicotinamide | I or VII | " | 1.0 g |
| 7 | N-(2-dodecylthio ethyl) p-butoxybenzamide | VII or IV | " | 1.0 g |
| 8 | N-(2-methylthio ethyl) p-toluenesulfonamide | VII or IV | " | 1.0 g |
| 9 | N-(2-isopropylthio ethyl) propionamide | VII or IV | " | 1.0 g |
| 10 | N-(2-octylthio ethyl) acetamide | VII or IV | " | 1.0 g |
| 11 | N-(2-butylthio ethyl) methanesulfonamide | VII or IV | " | 1.0 g |
| 12 | N-(2-isopentylthio ethyl)butane sulfonamide | VII or IV | " | 1.25 g |
| 13 | bis 1,4-(2-acetamido ethylthio) 2,3-butanediol | I or IV | " | 1.25 g |
| 14 | 2-hexadecylthio ethylamine hydrochloride | I or IV | " | 1.25 g |
| 16 | 2-allylthio ethylamine malate | I | Drops as in Ex. 27–34 | 1.25 g |
| 17 | 9-octadecene 2-ylthio ethylamine hydrochloride | I | " | 1.25 g |
| 18 | 2-dodecylthio ethylamine hydrochloride | I or IV | " | 1.25 g |
| 19 | 2-isopentylthio ethylamine mandelate | I or IV | " | 1.25 g |
| 20 | 2-octadecylthio ethylamine salicylate | I or IV | " | 1.50 g |
| 21 | 2-β-hydroxyethyl thio ethylurea | I or VIII | " | 1.50 g |
| 22 | 2-β-hydroxyethylthio ethylamine hydrochloride | I or IV | " | 1.50 g |
| 23 | 2-(2,3-dihydroxy propylthio)ethylamine p-toluenesulfonate | I or IV | " | 1.50 g |
| 24 | 2-(2-hydroxy propylthio)ethylamine oxalate | IV | " | 1.50 g |
| 25 | N-(2-methylthio ethyl)phenylacetamide | VII | " | 1.50 g |
| 26 | 2-(2,2-dimethoxy ethylthio) ethylamine hydrochloride | I | " | 1.50 g |
| 27 | 2-(2,2-dimethoxy ethylthio) ethylamine undecylenate | I | " | 2.0 g |
| 28 | 2-(2,2-diethoxy ethylthio) ethylamine undecylenate | I | " | 2.0 g |
| 29 | 2-(2,2-diethoxy ethylthio)ethylamine acetate | I | " | 2.0 g |
| 30 | 2-undecenylthio ethylamine | I | Drops as in Ex. 27–34 | 2.0 mg |
| 31 | 2-β-ureidoethylthio ethylamine hydrochloride | I or IV | " | 2.50 mg |
| 32 | 2-β-acetamidoethylthio ethylamine tropate | I or IV | " | 2.50 mg |
| 33 | 2,2'-thio diethylamine fumarate | I or IV | " | 3.0 mg |
| 34 | 2,2'-thio diethylurea | VIII or I | Ampoules as in Ex. 35–41 | 50 mg |
| 35 | 3-β-aminoethylthio propylamine hydrochloride | I or IV | " | 50 mg |
| 36 | S-β-ureidoethyl thiocarbamate | VIII | " | 50 mg |
| 37 | 2-ethoxycarbonylthio ethylamine hydrochloride | I | " | 50 mg |
| 38 | 2-dimethylamino carbonylthio ethylamine sulfate | I | " | 50 mg |
| 39 | 2-butoxycarbonyl methylthio ethylurea | I or IV | " | 50 mg |
| 40 | 2-ethyloxycarbonylmethylthio ethylamine hydrochloride | V | " | 50 mg |
| 41 | 6-β-aminoethylthio hexanoate of methyl hydrochloride | I | " | 50 mg |
| 42 | 5-β-aminoethylthio pentanoic acid | II | " | 50 mg |
| 43 | 2-phenylthio ethylamine dihydrogen phosphate | I or IV | " | 50 mg |
| 44 | 2-p-t-butylphenylthio ethylamine trichloracetate | I or IV | " | 50 mg |
| 45 | 2-p-methoxyphenylthio ethylamine ditartrate | I or IV | Ampoules as in Ex. 35–41 | 50 mg |
| 46 | 2-tolylthio ethylamine hydrobromide | I or IV | " | 50 mg |
| 47 | 2-(1-biphenyl thio) ethylamine hydrochloride | I or IV | " | 50 mg |
| 48 | 2-N-pentachlorophenylthio ethyl acetamide | I or IV | " | 50 mg |
| 49 | 2-benzylthio ethylamine malate | I or IV | " | 50 mg |
| 50 | 2-benzylthio ethylamine nicotinate | I or IV | " | 50 mg |

TABLE II-continued

| No. | Active Compound | Method of Preparation | Form of Composition | Amount in Composition |
|---|---|---|---|---|
| 51 | 2-benzylthio 2-methyl propylamine hydrochloride | I | '' | 50 mg |
| 52 | 2-benzylthio propylamine lactate | I | '' | 50 mg |
| 53 | N-(2-benzylthio ethyl)nicotinamide hydrochloride | VI | '' | 50 mg |
| 54 | N-(2-benzylthio ethyl) 10-undecene amide | VII or IV | '' | 50 mg |
| 55 | N-(2-benzylthio ethyl) hexadecanamide | VII or IV | '' | 50 mg |
| 56 | S-$\beta$-aminoethyl mercaptobutyric acid | I | '' | 50 mg |
| 57 | N-(2-benzylthio ethyl)formamide | VII | '' | 50 mg |
| 58 | N-(2-benzylthio ethyl)phenylacetamide | VII or IV | '' | 50 mg |
| 59 | N-[2-(2,6-dimethyl phenyl)ethyl] hexanamide | VII or IV | '' | 50 mg |
| 60 | 2-o-aminophenylthio ethylamine succinate | I or IV | Ampoules as in Ex. 35–41 | 50 mg |
| 61 | N-(2-benzylthio ethyl) glutamine | VII | '' | 50 mg |
| 62 | S-$\beta$-aminoethyl mercapto acetic acid | I | '' | 50 mg |
| 63 | (3-S-$\beta$-aminoethyl) mercapto propionic acid | II | '' | 50 mg |
| 64 | (3-S-$\gamma$-amino propyl) mercapto acetic acid | I | '' | 50 mg |
| 65 | S(2-p-methoxybenzamido ethyl) mercapto acetic acid | I | Lozenges as in Ex. 42–48 | 7.00 mg |
| 66 | 2-(2-naphtyl methylthio) ethylamine hydrochloride | I or IV | '' | 7.00 mg |
| 67 | 2-(2-naphtyl methylthio) ethylamine disuccinate | I or IV | '' | 7.00 mg |
| 68 | (2-thenyl) 2-thio ethylamine hydrobromide | I or IV | '' | 7.00 mg |
| 69 | 2-N-acetyl (2-thenylthio- ethylamine | VII or IV | '' | 7.00 mg |
| 70 | 2-o-chlorobenzylthio ethylamine hydrochloride | I or IV | '' | 15.0 mg |
| 71 | 2-p-chlorobenzylthio ethylamine glycolate | I or IV | '' | 15.0 mg |
| 72 | 2-o-fluorobenzylthio ethylamine hydrochloride | I or IV | '' | 15.0 mg |
| 73 | 2-furfurylthio ethylamine hydrochloride | I or IV | '' | 15.0 mg |
| 74 | 2-tetrahydrofurfurylthio ethylamine p-amino-benzoate | I or IV | '' | 15.0 mg |
| 75 | 2-$\beta$-phenylethylthio ethylamine glutamate | I or II | Lozenges as in Ex. 42–48 | 15.0 mg |
| 76 | 2-diphenylmethylthio ethylamine hydrochloride | I or III | '' | 17.5 mg |
| 77 | 2-triphenyl methylthio ethylamine hydrochloride hemihydrate | I or III | '' | 17.5 mg |
| 78 | 2-(2-pyridyl ethylthio)ethylamine hydrochloride | I or II | '' | 17.5 mg |
| 79 | 2-(2-p-toluene sulfonamido ethylthio) pyridine N-oxide | VII | '' | 17.5 mg |
| 80 | 2-$\beta$-aminoethylthiomethyl pyridine N-oxide dihydrochloride | I | '' | 17.5 mg |
| 81 | 2-$\beta$-aminoethylthio pyridine N-oxide hydrochloride | I | '' | 17.5 mg |
| 82 | 2,4-dichloro 2-benzylthio ethylamine aspartate | I or IV | '' | 20.0 mg |
| 83 | N-[2-(3,4-dichloro benzylthio)ethyl] butyramide | VII or IV | '' | 20.0 mg |
| 84 | N-[2-(2,6-dichloro benzylthio)ethyl] dodecanamide | VII or IV | '' | 20.0 mg |
| 85 | N-[2-(3,5-dichloro benzylthio)ethyl] trifluoroacetamide | VII or IV | '' | 20.0 mg |
| 86 | 2-o-methoxy benzylthio ethylamine hydrochloride | I or IV | '' | 20.0 mg |
| 87 | 2-p-ethoxybenzylthio ethylamine hydrochloride | I or IV | Lozenges as in Ex. 42–48 | 22.5 mg |
| 88 | N-[2-m-fluorobenzylthio ethyl] chloroacetamide | VII | '' | 22.5 mg |
| 89 | 2-p-bromobenzylthio ethylamine succinate | I or IV | '' | 22.5 mg |
| 90 | 2-(3,4-dimethoxy benzylthio)ethylamine malate | I or IV | '' | 22.5 mg |
| 91 | 2-(3,4-methylenedioxy benzylthio)ethylamine hydrochloride | I or IV | '' | 22.5 mg |
| 92 | 2-(2,4-dichloro cetylthio)ethylamine | | | |
| 93 | 2-(3,4,5-trimethoxy benzylthio)ethylamine hydrocinnamate | I or IV | '' | 25.0 mg |
| 94 | 2-p-methoxy benzylthio ethylamine salicylate | I or IV | '' | 25.0 mg |
| 95 | 2-o-methylbenzylthio ethylamine phenylacetate | I or IV | '' | 25.0 mg |
| 96 | N-[2-p-dimethylaminobenzylthio ethyl] methane-sulfonamide | VII or IV | '' | 25.0 mg |
| 97 | 2-p-phenoxybenzylthio ethylamine hydrochloride | I or IV | '' | 25.0 mg |
| 98 | 2-$\beta$-aminoethylthio pyridine hydrochloride | I or IV | Chewable pellets as in Ex. 49–53 | 1.90 g |
| 99 | 2-benzylthio ethylamine citrate | I or IV | Chewable pellets as in Ex. 49–53 | 1.90 g |
| 100 | N-[2-benzylthio ethyl] 2,4-dihydroxy 3,3-dimethyl butyramide | VII | '' | 1.90 g |
| 101 | N-(2-benzylthio ethyl) 6,8-dihydroxy 7,7-dimethyl 5-oxo 4-aza octanamide | VII | '' | 1.90 g |

TABLE II-continued

| No. | Active Compound | Method of Preparation | Form of Composition | Amount in Composition |
|---|---|---|---|---|
| 102 | N-[2-(2-pyridyl thio)ethyl] propionamide | VII or IV | " | 1.90 g |
| 103 | 2-(2-pyridyl methylthio)ethylamine dihydrochloride | I | " | 2.5 g |
| 104 | 2-benzylthio ethylamine pantothenate | I or IV | " | 2.5 g |
| 105 | S-($\beta$-acetamidoethyl)mercaptoacetate of $\beta$-morpholinoethyl | V or IV | " | 2.5 g |
| 106 | S-($\beta$-phenylacetamidoethyl)mercaptoacetate of N'-methyl 2-piperazino ethyl | V or IV | " | 2.5 g |
| 107 | S-($\beta$-ureidoethyl)mercaptoacetate of $\beta$-pyrrolidino-ethyl | V | " | 2.5 g |
| 108 | S-($\beta$-trifluoroacetamidoethyl)-$\beta$mercapto-propionate of $\beta$-dimethylaminoethyl | V | " | 3.75 g |
| 109 | 2-p-nitrobenzylthio ethylamine crotonate | I or IV | " | 3.75 g |
| 110 | 2-$\beta$-morpholinocarbonyl ethylthio ethylamine hydrochloride | I or II | " | 3.75 g |
| 111 | N,N-di(hydroxyethyl)S-($\beta$-benzamido-ethyl)mercapto-acetamido | I or IV | Chewable pellets as in Ex. 49–53 | 3.75 g |
| 112 | N[2-N'-methyl piperazino carbonylthio ethyl] acetamide | I | " | 3.75 g |
| 113 | 2-(1-naphthyl thio)ethylamine hydrochloride | I or IV | " | 3.75 g |
| 114 | N-(3-$\beta$-ureidoethylthio propyl) succinamic acid | VII | " | 5.0 g |
| 115 | 3-allylthio propylamine | I | " | 5.0 g |
| 116 | 3-(2,2'-dimethoxy ethylthio)propylamine | I | " | 5.0 g |
| 117 | 3-(2,2'-dimethoxy ethylthio)propylamine sulfate | VII or IV | " | 5.0 g |
| 118 | S-$\beta$-aminoethylmercapto acetic acid | VII or IV | " | 5.0 g |
| 119 | The hydrochloride of S-$\beta$-aminoethyl mercapto acetic acid | VII or IV | " | 5.0 g |
| 120 | N-(2-benzylthioethyl)acetamide | VII or IV | " | 6.25 g |
| 121 | N-(2-benzylthioethyl)propionamide | VII or IV | " | 6.25 g |
| 122 | N-(2-benzylthioethyl)butyramide | VII or IV | " | 6.25 g |
| 123 | N-(2-benzylthioethyl)methanesulfonamide | VII or IV | " | 6.25 g |
| 124 | N-(2-benzylthioethyl)ethanesulfonamide | VII or IV | " | 6.25 g |
| 125 | N-(2-benzylthioethyl-propanesulfonamide | VII or IV | " | 7.50 g |
| 126 | N-(2-benzylthioethyl)butanesulfonamide | VII or IV | Chewable pellets as in Ex. 49–53 | 7.50 g |
| 127 | S-(2-p-acetamidobenzenesulfonamido ethyl) mercapto acetic acid | I or IV | " | 7.50 g |
| 128 | S-(2-p-acetamidobenzamido ethyl) mercapto acetic acid | I or IV | " | 7.50 g |
| 129 | N-(2-thenylthioethyl)acetamide | VII or I | " | 7.50 g |
| 130 | 2-benzylthio propylamine | I | " | 7.50 g |
| 131 | 2-benzylthio 2-methyl propylamine | I | Tablets as in Ex. 54–56 | 6. mg |
| 132 | 2-(2-p-toluenesulfonamido ethylthio) pyridine N-oxide | VII | " | 6. mg |
| 133 | S-(2-p-butoxybenzamidoethyl)mercapto acetic acid | I or IV | " | 6. mg |
| 134 | 2-t-butylthio ethylamine hydrochloride | III | " | 6. mg |
| 135 | 2-methoxycarbonyl methylthio ethylamine hydrochloride | V | " | 6. mg |
| 136 | 2-ethoxycarbonylmethylthio ethylamine hydrochloride | V | " | 10. mg |
| 137 | 2-propoxycarbonylmethyl thio ethylamine hydrochloride | V | " | 10. mg |
| 138 | 2-butoxycarbonylmethylthio ethylamine hydrochloride | V | " | 10. mg |
| 139 | 2,2'-thio diethylamine dihydrochloride | I or IV | Tablets as in Ex. 54–56 | 10. mg |
| 140 | 3-(2-aminoethylthio)alanine hydrochloride | I or IV | " | 10. mg |
| 141 | 2-benzylthio ethylammonium diacid phosphate | I or IV | " | 12.5 mg |
| 142 | 2-methylthio ethylamine | I or IV | " | 12.5 mg |
| 143 | N-(methylthioethyl) p-acetamidobenzamide | VII or IV | " | 12.5 mg |
| 144 | N-(2-methylthioethyl)nicotinamide | " | " | 12.5 mg |
| 145 | N-(2-methylthioethyl)benzamide | " | " | 15. mg |
| 146 | N-(2-methylthioethyl) p-methoxybenzamide | " | " | 15. mg |
| 147 | N-(2-methylthioethyl) p-butoxybenzamide | " | " | 15. mg |
| 148 | N-(2-methylthioethyl) butyramide | " | " | 15. mg |
| 149 | N-(2-methylthioethyl) propionamide | " | " | 15. mg |
| 150 | N-(2-methylthioethyl) acetamide | " | " | 17.5 mg |
| 151 | N-(2-methylthioethyl) butanesulfonamide | " | " | 17.5 mg |
| 152 | N-(2-octylthioethyl) methanesulfonamide | " | " | 17.5 mg |
| 153 | 2-cetylthio ethylamine hydrochloride | I | " | 17.5 mg |
| 154 | 2-(2-hydroxyethylthio) ethylamine hydrochloride | I or IV | " | 17.5 mg |
| 155 | 2-methylthio ethylamine phenylacetate | I or IV | " | 20. mg |
| 156 | 2-methylthio ethylamine undecylenate | I or IV | " | 20. mg |

What is claimed is:

1. A method for treating a scalp, characterized by an excessive secretion of sebum, to improve the condition thereof by reducing said excessive secretion of sebum comprising orally administering to a human being having a scalp so characterized a therapeutic composition comprising an ingestible carrier admixed with a nontoxic active compound selected from the group consisting of 2-methylthio ethylamine cinnamate,
2-hexadecylthio ethylamine hydrochloride,
2-allylthio ethylamine malate,
9-octadecene-2-ylthio ethylamine hydrochloride,
2-dodecylthio ethylamine hydrochloride,
2-isopentylthio ethylamine mandelate,
2-octadecylthio ethylamine salicylate,
2-β-hydroxyethylthio ethylamine hydrochloride,
2-(2,3-dihydroxy propylthio) ethylamine p-toluenesulfonate,
2-(2-hydroxy propylthio) ethylamine oxalate,
2-(2,2-dimethoxy ethylthio) ethylamine hydrochloride,
2-(2,2-dimethoxy ethylthio) ethylamine undecylenate,
2-(2,2-diethoxy ethylthio) ethylamine undecylenate,
2-(2,2-diethoxy ethylthio) ethylamine acetate,
2-undecenylthio ethylamine,
2-β-acetamidoethylthio ethylamine tropate,
2,2′-thio diethylamine fumarate,
3-β-aminoethylthio propylamine hydrochloride,
3-allylthio propylamine,
3-(2,2′-dimethoxy ethylthio) propylamine,
3-(2,2′-dimethoxy ethyl thio) propylamine sulfate,
2-t-butylthio ethylamine hydrochloride,
2,2′-thio diethylamine dihydrochloride,
2-methylthio ethylamine,
2-cetylthio ethylamine hydrochloride,
2-methylthio ethylamine phenylacetate and
2-methylthio ethylamine undecylenate,
said active compound being present in an amount ranging from 0.75 to 3 percent by weight of said composition and said composition being administered at a rate of 1–5 mg/kg/day based on the weight of the human being.

2. The method of claim 1 wherein said active compound is 2-methylthio ethylamine phenylacetate.

* * * * *